United States Patent
Heafield et al.

Patent Number: 5,091,189
Date of Patent: Feb. 25, 1992

[54] CONTROLLED RELEASE DOSAGE FORMS HAVING A DEFINED WATER CONTENT

[75] Inventors: Joanne Heafield; Stewart I. Leslie; Sandra T. A. Malkowska; Philip J. Neale, all of Cambridge, United Kingdom

[73] Assignee: Euroceltique S.A., Luxembourg, Luxembourg

[21] Appl. No.: 704,714

[22] Filed: May 17, 1991

Related U.S. Application Data

[63] Continuation of Ser. No. 355,417, May 23, 1989, abandoned.

[30] Foreign Application Priority Data

Jun. 2, 1988 [GB] United Kingdom ............... 8813064

[51] Int. Cl.$^5$ ................................. A61K 9/52
[52] U.S. Cl. .................... 424/457; 424/455; 424/459; 424/468
[58] Field of Search ............... 424/457, 458, 459, 468

[56] References Cited

U.S. PATENT DOCUMENTS

| | | | |
|---|---|---|---|
| 3,965,256 | 6/1976 | Leslie | 424/22 |
| 4,743,247 | 5/1988 | Wong | 424/468 |
| 4,753,800 | 6/1988 | Mozda | 424/440 |
| 4,844,910 | 7/1989 | Leslie et al. | 424/470 |

FOREIGN PATENT DOCUMENTS

| | | |
|---|---|---|
| 97523 | 1/1984 | European Pat. Off. . |
| 109320 | 6/1986 | European Pat. Off. . |
| 251459 | 1/1988 | European Pat. Off. . |
| 270305 | 6/1988 | European Pat. Off. . |

*Primary Examiner*—Thurman K. Page
*Assistant Examiner*—Leon R. Horne
*Attorney, Agent, or Firm*—Nixon & Vanderhye

[57] ABSTRACT

A controlled release, solid, oral dosage form containing a 3-alkylxanthine, preferably theophylline, at least one hydrophilic or hydrophobic polymer, at least one wax having a melting point between 25° and 90° C. and between 3% and 10% (by weight) water.

Preferably the dosage form is a tablet and the water content is between 4% and 9% (by weight). The amount of water present in the dosage form determines the rate of release of the 3-alkylxanthine.

23 Claims, No Drawings

CONTROLLED RELEASE DOSAGE FORMS HAVING A DEFINED WATER CONTENT

This is a continuation of application Ser. No. 07/355,417, filed May 23, 1989, now abandoned.

The present invention relates to a controlled release, oral dosage form, especially a tablet, containing a 3-alkylxanthine.

It is one object of the present invention to provide a 3-alkylxanthine containing controlled release, oral dosage form having a narrow range of in-vitro dissolution rates over a wide pH range (pH 1.6 to 7.2). Other objects and advantages of the present invention will become apparent from the following detailed description thereof.

According to the present invention, there is provided a controlled release, solid, oral dosage form comprising a 3-alkylxanthine, at least one hydrophilic or hydrophobic polymer, at least one wax having a melting point between 25° C. and 90° C. and between 3% and 10% (by weight) water.

Oral dosage forms according to the present invention are preferably tablets but are not spheroids, film coated spheroids or unit dosage forms (e.g. capsule, sachet, cachet) containing spheroids or film coated spheroids.

In the present specification "per cent (by weight) water" refers to the water content of the oral dosage form as measured using a Karl Fischer titration method.

Preferably the water content of the oral dosage form is between 4% and 9% (by weight), most preferably between 4% and 8% (by weight), especially between 5% and 7% (by weight). A particularly preferred oral dosage form according to this invention has a water content of about 6% (by weight).

The present inventors have surprisingly found that the water content of the present dosage forms has a dramatic effect on the in-vitro release rate of the active ingredient. When the water content of the dosage forms is below 3% (by wt), the release rate is too slow. When the water content of the dosage forms is above 10%, the release rate is too fast.

Furthermore, when the dosage forms have a water content between 3% and 10% (by wt) they (the dosage forms) are more stable over a 1-2 year period (with regard to rate of release of the active ingredient) than other equivalent dosage forms having water contents outside this range.

It is a particular advantage of the present dosage forms that the in-vitro dissolution rate is substantially independent of pH over a wide range (1.6 to 7.2).

The present controlled release dosage forms contain a 3-alkylxanthine. The phrase "3-alkylxanthine" in the present specification incorporates (i) Any xanthine substituted at the 3 nitrogen by an alkyl group, and
(ii) Any salt or derivative of such a 3-alkyl substituted xanthine.

Thus, the 3-alkylxanthine may be, for example, emprofylline or theobromine. Preferably, however, the 3-alkylxanithine is a 1,3-dimethylxanthine, such as acepifylline, bamifylline, bufylline, diprophylline, etamiphylline, etofylline, proxyphylline or theophylline. Of these 1,3-dimethyl xanthines, theophylline (anhydrous or hydrate) or a salt or derivative of theophylline, such as aminophylline, choline theophyllinate, theophylline monoethanolamine, theophylline sodium glycinate or theophylline calcium salicylate is particularly preferred. Theophylline (anhydrous or hydrate) is the most preferred.

When theophylline is the 3-alkylxanthine, the in vitro dissolution rate of the theophylline from the present oral dosage form, when measured by the USP Paddle Method at 100 rpm in 900 ml aqueous buffer (pH 6.5) at 37° C. is preferably between 5% and 30% (by wt) release after 2 hours,
between 15% and 40% (by wt) release after 4 hours,
between 20% and 55% (by wt) release after 6 hours,
between 25% and 65% (by wt) release after 8 hours, and
between 40% and 90% (by wt) release after 12 hours.

Preferred doses of the 3-alkylxanthines in a controlled release dosage form according to this invention are as follows:

| | |
|---|---|
| Acepifylline | 125–1000 mg |
| Aminophylline | 50–450 mg |
| Bamifylline HCl | 150–600 mg |
| Bufylline | 30–120 mg |
| Choline Theophyllinate | 50–400 mg |
| Diprophylline | 50–400 mg |
| Enprofylline | 50–600 mg |
| Etamiphylline camsylate | 50–600 mg |
| Etofylline | 100–600 mg |
| Proxyphylline | 100–600 mg |
| Theobromine | 50–600 mg |
| Theophylline | 50–600 mg |
| Theophylline Monoethanolamine | 50–400 mg |
| Theophylline Na Glycinate | 50–600 mg |

The concentration of 3-alkylxanthine in the present dosage forms will depend, amongst other factors, on the amount of xanthine to be administered. In the case of theophylline, the dosage forms preferably contain between 40% and 85% (by wt), especially between 50% and 80% (by wt), of the active ingredient. The at least one hydrophilic or hydrophobic polymer may be chosen from such materials as gums, cellulose ethers, acrylic resins and protein derived materials. Of these polymers, the cellulose ethers, especially hydroxyalkylcelluloses and carboxyalkylcelluloses, are preferred. The oral dosage form may contain between 1% and 20%, especially between 2% and 12% (by weight) of the at least one hydrophilic or hydrophobic polymer.

The at least one wax of the present invention must have a melting point between 25° C. and 90° C., preferably between 40° and 70°. The at least one wax may be, for example, a polyalkylene glycol, a fatty (aliphatic) acid, a fatty (aliphatic) ester or, which is preferred, a fatty (aliphatic) alcohol, particularly a $C_{12}$–$C_{36}$ fatty alcohol, especially a $C_{14}$–$C_{22}$ fatty alcohol such as myristyl alcohol, cetyl alcohol, stearyl alcohol or cetostearyl alcohol. The present dosage forms preferably contain between 4% and 40%, especially between 8% and 36%, by weight of the at least one wax.

One particularly suitable dosage form according to this invention comprises a 3-alkylxanthine, a water-soluble hydroxyalkyl cellulose, at least one $C_{12}$–$C_{36}$, preferably $C_{14}$–$C_{22}$, fatty alcohol and, optionally, at least one polyalkylene glycol.

The at least one hydroxyalkyl cellulose is preferably a hydroxy ($C_1$ to $C_6$) alkyl cellulose, such as hydroxypropycellulose, hydroxypropylmethylcellulose and especially, hydroxyethyl cellulose. The amount of the at least one hydroxyalkyl cellulose in the present dosage form will be determined, inter alia, by the precise rate of drug release required. Preferably, however, the dosage form contains between 1% and 20%, especially between 2% and 12% (by weight) of the at least one hydroalkyl cellulose.

The at least one fatty alcohol may be, for example, lauryl alcohol, myristyl alcohol or stearyl alcohol. In particularly preferred embodiments of the present dosage form, however, the at least one fatty alcohol is cetyl alcohol or cetostearyl alcohol. The amount of the at least one fatty alcohol in the present dosage form will be determined, as above, by the precise rate of drug release required. It will also depend on whether at least one polyalkylene glycol is present in or absent from the dosage form. In the absence of at least one polyalkylene glycol, the dosage form preferably contains between 4% and 40%, especially between and 8% and 36%, (by weight) of the at least one fatty alcohol. When at least one polyalkylene glycol is present in the dosage form then the combined weight of the at least one fatty alcohol and the at least one polyalkylene glycol preferably constitutes between 4% and 40%, especially between 8% and 36%, (by weight) of the total dosage form weight.

In the present preferred dosage form, the ratio of the at least one hydroxyalkyl cellulose to the at least one fatty alcohol/polyalkylene glycol determines, to a considerable extent, the release rate of the drug from the formulation. A ratio of the at least one hydroxyalkyl cellulose to the at least one fatty alcohol/polyalkylene glycol of between 1:2 and 1:4 is preferred, with a ratio of between 1:3 and 1:4 being particularly preferred.

The at least one polyalkylene glycol may be, for example, polypropylene glycol or, which is preferred, polyethylene glycol. The number average molecular weight of the at least one polyalkylene glycol is preferably between 1000 and 15000 especially between 1500 and 12000.

Another suitable controlled release dosage form would comprise a 3-alkylxanthine, an alkylcellulose (especially ethyl cellulose), a $C_{12}$ to $C_{36}$ fatty alcohol and, optionally, a polyalkylene glycol.

In addition to the above ingredients, a controlled release dosage form according to this invention may also contain suitable quantities of other materials, e.g. diluents, lubricants, binders, granulating aids, colourants, flavourants and glidants that are conventional in the pharmaceutical art. In order to facilitate the preparation of a controlled release dosage form according to this invention there is provided, in a further aspect of the present invention, a process for the preparation of a controlled release, solid, oral dosage form according to the present invention comprising (a) wet granulating water, at least one hydrophilic or hydrophobic polymer and a 3-alkylxanthine to form granules,
(b) drying the granules,
(c) mixing the 3-alkylxanthine containing granules with at least one wax having a melting point between 25° and 90° C., and
(d) optionally, compressing and shaping the granules, wherein the granules are dried to such an extent that the controlled release, solid, oral dosage form contains between 3% and 10% (by weight) water.

In a preferred embodiment of this process, the amount of water (including water of crystallisation) added during the wet granulation step is preferably between 2 and 30 times, especially between 4 and 20 times, the dry weight of the hydrophilic or hydrophobic polymer.

The present controlled release dosage form and processes for the preparation of such dosage forms will now be described by way of example only:

DETERMINATION OF WATER CONTENT BY THE KARL FISCHER METHOD

1. A Karl Fischer Autotitration unit (Baird and Tatlock) was set up according to the manufacturer's instructions.
2. A sample volume of Karl Fischer reagent (Fisons) was standardised.
3. A predetermined quantity of tablets was ground to a fine powder in a mortar and pestle.
4. Approximately 0.5 g of the powdered tablets was weighed into the sample vessel.
5. The Karl Fischer reagent was neutralised in the reaction vessel and then the sample was added. The mixture was stirred for 3minutes.
6. The sample vessel was reweighed in order to determine the weight of sample used.
7. A Karl Fischer titration was then carried out in the reaction vessel, the amount of titrant added being noted. The test was carried out in duplicate.

EXAMPLE 1

Theophylline monohydrate (330 gm) and hydroxyethyl cellulose (18.5 gm) were dry mixed. Povidone (3.75 gm) was then dissolved in water (40 ml) and the solution, together with a further 60 ml of water, was added to the theophylline mixture. The whole was then granulated, subsequently dried in a fluid bed drier (FBD) and then sieved through a 12 mesh screen. After sieving, the granules were again dried and sieved again, this time through a 16 mesh screen. The granules were then cooled.

Cetostearyl alcohol (30 gm) and polyethylene glycol (PEG) 6000 (37.5 gm) were mixed and heated to give a molten mixture. The wax/PEG 6000 mixture was then added to the granules and granulated. The wax coated granules were cooled and sieved through a 16 mesh screen. Finally, the wax coated granules were blended with magnesium stearate (7.5 gm) and talc (7.5 gm) and compressed to give 1000 tablets, each having the following formulation,

|  | mg/tablet |
|---|---|
| Theophylline monohydrate | 330.0 |
| Hydroxyethyl cellulose | 18.5 |
| Povidone | 3.75 |
| Cetostearyl alcohol | 30.0 |
| Polyethylene glycol 6000 | 37.5 |
| Magnesium stearate | 7.5 |
| Talc | 7.5 |

The water content of these tablets (by Karl Fischer) was 5.5% (by weight of the total tablet weight).

EXAMPLE 2

The procedure of Example 1 was followed to give 1000 tablets, each having the following formulation,

|  | mg/tablet |
|---|---|
| Theophylline monohydrate | 220.0 |
| Hydroxyethyl cellulose | 12.5 |
| Povidone | 2.5 |
| Cetostearyl alcohol | 20.0 |
| Polyethylene glycol 6000 | 10.0 |
| Magnesium stearate | 5.0 |

| | mg/tablet |
|---|---|
| Talc | 5.0 |

The water content of these tablets (by Karl Fischer) was 5.9% (by weight of the total tablet weight).

EXAMPLE 3

The procedure of Example 1 was followed to give 1000 tablets, each having the following formulation,

| | mg/tablet |
|---|---|
| Theophylline monohydrate | 440.0 |
| Hydroxyethyl cellulose | 25.0 |
| Povidone | 5.0 |
| Cetostearyl alcohol | 40.0 |
| Polyethylene glycol 6000 | 50.0 |
| Magnesium stearate | 10.0 |
| Talc | 10.0 |

The water content of these tablets (by Karl Fischer) was 6.5% (by weight) of the total tablet weight).

EXAMPLE 4

The procedure of Example 2 was followed except that the tablets had a water content (by Karl Fischer) of 8.1% (by weight of the total tablet weight).

EXAMPLE 5

The procedure of Example 2 was followed except that the tablets had a water content (by Karl Fischer) of 9.7% (by weight of the total tablet weight).

The dissolution of tablets prepared according to Examples 2, 4 and 5 was measured at 37° C. by the USP Paddle Method in USP Buffer (900 ml, pH 6.5) at 100 rpm. Results are given in Table 1.

TABLE 1

| EXAMPLE | 2 | 4 | 5 |
|---|---|---|---|
| 1 Hour | 14.4 | 16.5 | 18.4 |
| 2 Hours | 22.6 | 26.6 | 29.1 |
| 4 Hours | 36.3 | 42.9 | 45.2 |
| 6 Hours | 47.0 | 55.0 | 59.4 |
| 8 Hours | 57.4 | 66.2 | 71.3 |
| 10 Hours | 66.9 | 76.5 | 81.6 |
| 12 Hours | 76.2 | 86.2 | 91.3 |
| 14 Hours | 85.0 | 94.0 | 97.5 |

We claim:

1. A controlled release, solid, oral dosage form comprising a 3-$C_{1-3}$ alkylxanthine, at least one hydrophilic or hydrophobic polymer, from between 4% and 40% by weight of at least one wax having a melting point between 20° and 90° C., and between 3% and 10% by weight water, said dosage from excluding spheroids, film coated spheroids or unit dosage forms containing spheroids or film coated spheroids.

2. An oral dosage form according to claim 1 containing between 4% and 9% (by weight) water.

3. An oral dosage form according to claim 2 containing between 4% and 8% (by weight) water.

4. An oral dosage form according to claim 3 containing between 5% and 7% (by weight) water.

5. An oral dosage form according to claim 1 wherein the 3-alkylxanthine comprises a 1,3-dimethylxanthine.

6. An oral dosage form according to claim 5 wherein the 1,3-dimethylxanthine is selected from the group consisting of acepifylline, bamifylline, bufylline, diprophylline, etamiphylline, etophylline, proxyphylline and theophylline.

7. An oral dosage form according to claim 6 wherein the 1,3-dimethylxanthine comprises theophylline.

8. An oral dosage form according to claim 7 wherein the dosage form contains between 40% and 85% (by weight) theophylline.

9. An oral dosage form according to claim 8 wherein the dosage form contains between 50% and 80% (by weight) theophylline.

10. An oral dosage form according to claim 1 wherein the dosage form contains between 1% and 20% (by weight) of the at least one hydrophilic or hydrophobic polymer.

11. An oral dosage form according to claim 10 wherein the dosage form contains between 2% and 12% (by weight) of the at least one hydrophilic or hydrophobic polymer.

12. An oral dosage form according to claim 1 wherein the at least one hydrophilic or hydrophobic polymer comprises a cellulose ether.

13. An oral dosage form according to claim 12 wherein the cellulose ether comprises a hydroxyalkylcellulose or a carboxyalkylcellulose.

14. An oral dosage form according to claim 13 wherein the hydroxyalkylcellulose is selected from the group consisting of hydroxypropylcellulose, hydroxypropylmethylcellulose and hydroxyethylcellulose.

15. An oral dosage form according to claim 14 wherein the hydroxyalkylcellulose comprises hydroxyethylcellulose.

16. An oral dosage form according to claim 1 wherein the dosage form contains between 4% and 40% (by weight) of the at least one wax.

17. An oral dosage form according to claim 1 wherein the dosage form contains between 8% and 36% (by weight) of the at least one wax.

18. An oral dosage form according to claim 1 wherein the at least one wax comprises a wax having a melting point between 40° and 70° C.

19. An oral dosage form according to claim 1 wherein the at least one wax is selected from the group consisting of a polyalkylene glycol having an average molecular weight of between 1,000 and 15,000, a fatty acid, a fatty acid ester and a fatty alcohol.

20. An oral dosage form according to claim 19 wherein the fatty alcohol comprises a $C_{12}$–$C_{36}$ fatty alcohol.

21. An oral dosage form according to claim 20 wherein the fatty alcohol comprises a $C_{14}$–$C_{22}$ fatty alcohol.

22. An oral dosage form according to claim 21 wherein the fatty alcohol is selected from the group consisting of myristyl alcohol, cetyl alcohol, stearyl alcohol and cetostearyl alcohol.

23. A controlled release, solid, oral dosage form according to claim 1 wherein the oral dosage form is a tablet.

* * * * *